(12) United States Patent
Wu et al.

(10) Patent No.: US 10,729,451 B2
(45) Date of Patent: Aug. 4, 2020

(54) UNIVERSAL OSTEOTOMY DEVICE

(71) Applicant: A Plus Biotechnology Company Limited, New Taipei (TW)

(72) Inventors: Kai-Hsing Wu, Taipei (TW); Hsiang-Wei Lo, New Taipei (TW); Kun-Jhih Lin, Taichung (TW); Ping-Sheng Yu, Taipei (TW)

(73) Assignee: A PLUS BIOTECHNOLOGY COMPANY LIMITED, New Taipei (TW)

( * ) Notice: Subject to any disclaimer, the term of this patent is extended or adjusted under 35 U.S.C. 154(b) by 241 days.

(21) Appl. No.: 15/927,109

(22) Filed: Mar. 21, 2018

(65) Prior Publication Data
US 2019/0150949 A1    May 23, 2019

(30) Foreign Application Priority Data

Nov. 22, 2017   (TW) .............................. 106140620 A

(51) Int. Cl.
| | | |
|---|---|---|
| *A61B 17/15* | (2006.01) | |
| *A61B 17/17* | (2006.01) | |
| *A61B 17/80* | (2006.01) | |
| *A61B 90/50* | (2016.01) | |

(52) U.S. Cl.
CPC .......... *A61B 17/157* (2013.01); *A61B 17/152* (2013.01); *A61B 17/1764* (2013.01); *A61B 17/155* (2013.01); *A61B 17/80* (2013.01); *A61B 90/50* (2016.02)

(58) Field of Classification Search
CPC .. A61B 17/157; A61B 17/152; A61B 17/1764
See application file for complete search history.

(56) References Cited

U.S. PATENT DOCUMENTS

| | | | |
|---|---|---|---|
| 2012/0310246 A1* | 12/2012 | Belcher ................ | A61B 17/155 606/80 |
| 2013/0150862 A1* | 6/2013 | Aram ................... | A61B 17/157 606/88 |
| 2016/0051268 A1* | 2/2016 | Seitlinger .......... | A61B 17/1764 606/88 |

\* cited by examiner

*Primary Examiner* — Christian A Sevilla
(74) *Attorney, Agent, or Firm* — Muncy, Geissler, Olds & Lowe, P.C.

(57) ABSTRACT

The present invention provides a universal osteotomy device comprising a first body component and a second body component. The first body component has an upper guide edge for forming a cutting track. The second body component has a lower guide edge disposed below the upper guide edge. A guide slot is formed between the upper guide edge and the lower guide edge for guiding the saw blade to cut. The guide slot has a connecting member for connecting the upper guide edge and the lower guide edge. The surface of the first body component and the surface of the second body component have an average curvature of the bone surface.

10 Claims, 8 Drawing Sheets

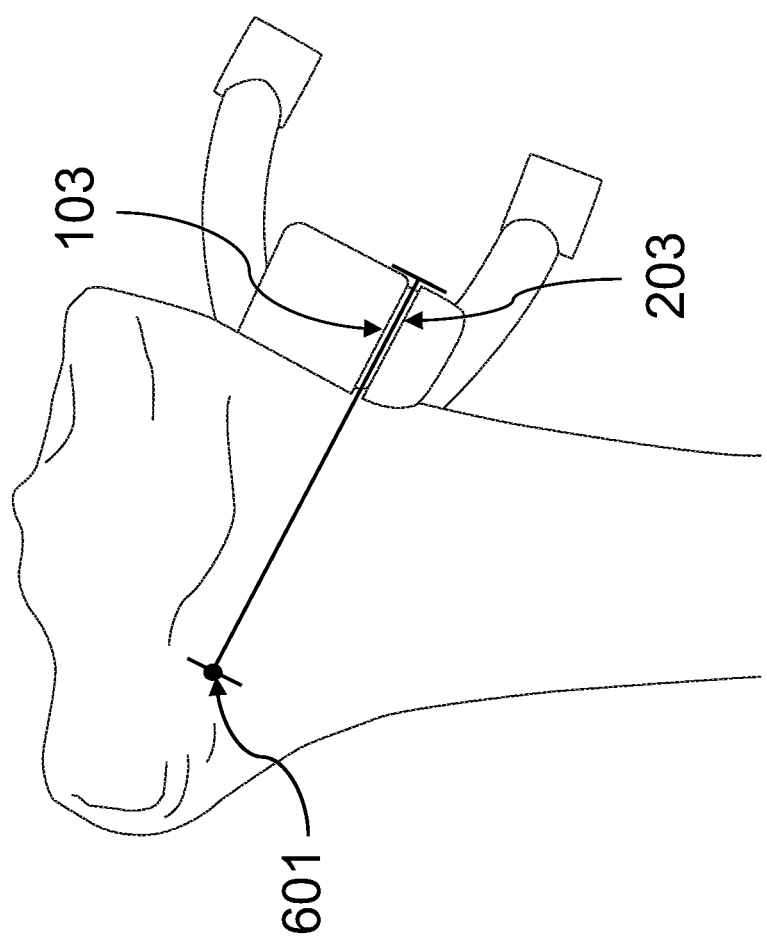

UNIVERSAL OSTEOTOMY DEVICE

BACKGROUND OF THE INVENTION

Technical Field

The present invention generally relates to an osteotomy device, and more particularly, to a universal osteotomy device.

Description of Related Art

Under the continuous development of science and technology, human average life-span continues to be extended. But the articular cartilage is gradually worn with the aging of body. It causes the occurrence of degenerative joint disease called osteoarthritis. For patients with knee osteoarthritis in the observation of the X-ray, surgeons can find the uneven of joint surface, narrowed joint cavity and bone spurs. These pathological phenomena will cause the patients to produce pain, swelling, joint deformation, stiffness and other symptoms. This is the inevitable trend of physiological aging, it seems that the older the more likely to encounter the disease.

Taking knee for example, most common treatment of knee osteoarthritis is to implant the artificial joint to replace the knee joint surface, but large amount of soft tissue and hard tissue should be removed from the femur, the tibia and the patella to provide the fixation of metal and polyethylene implants. Due to the wear of the polyethylene component, the longevity of the artificial joint replacement is up to twenty years, but often complicated by postoperative infection, osteolysis and bone resorption. Resulting in the possibility of a revision surgery. Furthermore, in early-stage knee osteoarthritis, only the medial articular surface is affected. It is not necessary to replace all articular surface by artificial knee components. High tibial osteotomy is an alternative option for patients with medial knee osteoarthritis.

High tibial osteotomy is performed by a bony cutting plane in the proximal tibia of the knee on the medial side and making a wedge space by opening the osteotomy. Finally, the construct is supported by bone plate fixation. Thus the biomechanical axis of the low limb can be corrected. In this procedure, the cartilage and bone stock around the knee are preserved. For the patients with medial knee osteoarthritis, it is a good option for surgical treatment.

The success for high tibial osteotomy relies on an appropriate bone cut including the cutting position, direction, depth, and spreading height which are related to the correction angle. This surgery is highly technical demanded. At present, the surgeons perform the procedure based upon preoperative roentgenology images and their experience without any reference or guiding device. The above-mentioned parameters are also different for each patient.

However, if the overall osteotomy device was designed in accordance with the needs of patients, even though it has a customized geometry and design parameters and fully meet the needs of patients and other advantages, but it will take a long time for design estimation, a long time for manufacturing before surgery and other shortcomings. It may not be possible to provide immediate treatment in some emergency situations that are time-limited. Therefore, it may miss the critical period. So, how to allow the surgeons can perform an accurate, rapid and convenient operation for joint osteotomy, it is an important issue, too.

The prior art of the present invention is TWM536526U. But, there is still room for improvement. For examples, it cannot take a non-invasive assessment of the correction angle when the surgery is performed, it cannot predict whether the placement (orientation/position) of the osteotomy device is correct, it cannot directly fix the placement of the osteotomy device, it may result in over-cutting, it may require preoperative evaluation for the patient's curvature of the bone surface, it cannot be applied to the need for urgent surgery and the manufacturing process is complicated. The inventor of the present invention has further expanded its function and improved many of the techniques present in the prior art. Therefore, the inventor developed the universal osteotomy device, the expansion of the function and improvement of the technology will be described in detail in the specification.

SUMMARY OF THE INVENTION

In view of the foregoing problems, the present invention provides a universal osteotomy device. It is used to guide a saw blade to perform high tibial osteotomy of tibia, but not limited to, the universal osteotomy device can be used for other bones, such as: femur, fibula, humerus, ulna, radius, clavicle, scapula and so on. The tibia is described in the preferred embodiment of the present invention. The device design features to assist the surgeon to determine the cutting position, direction, depth and the spreading height of the osteotomy precisely, rapidly and conveniently. Moreover, it can take a non-invasive assessment of the correction angle when the surgery is performed, it can predict whether the orientation/position of the osteotomy device placement is correct, it can directly maintain the orientation/position of the osteotomy device placement, and it can avoid over-cutting, it does not require preoperative evaluation for the curvature of the bone surface, it can be applied to the need for urgent surgery and the manufacturing process is simple. The osteotomy of the tibia after the operation of the present invention will have the precise cutting angle, the accuracy and the efficiency of the implementation. It can also be used for emergencies that are time-limited.

The present invention provides a universal osteotomy device. The universal osteotomy device is used to guide a saw blade to perform high tibial osteotomy, but not limited to, it can also be applied to other bones. The universal osteotomy device comprises: a first body component and a second body component. Wherein the first body component has an upper guide edge for forming a cutting track; the second body component has a lower guide edge disposed below the upper guide edge, a guide slot is formed between the upper guide edge and the lower guide edge for guiding a saw blade to perform an osteotomy procedure. The guide slot has a connecting member for connecting the upper guide edge and the lower guide edge. Wherein the surface of the first body component and the surface of the second body component have an average curvature or a uniform curvature of the bone surface.

According to the embodiment of the present invention, the universal osteotomy device comprises: a first body component, a second body component and an extracorporeal alignment component. Wherein the first body component has an upper guide edge for forming a cutting track; the second body component has a lower guide edge disposed below the upper guide edge, a guide slot is formed between the upper guide edge and the lower guide edge for guiding a saw blade to perform a cutting procedure. The guide slot has a connecting member for connecting the upper guide edge and the lower guide edge. The extracorporeal alignment component has an engaging member and at least one aiming hole. The engaging member is engaged with the connecting member. The aiming hole is used to confirm the direction of cutting. Wherein the surface of the first body component and the surface of the second body component have an average curvature or a uniform curvature of the bone surface.

According to the embodiment of the present invention, the first body component has an upper guide edge and a side guide edge. The side guide edge is disposed at the end of the upper guide edge for forming a cutting track.

According to the embodiment of the present invention, the second body component has a lower guide edge and an extended barrier plate. The lower guide edge disposed below the upper guide edge. The extended barrier plate is disposed at the end of the lower guide edge to prevent over-cutting by the saw blade on the side guide edge. A guide slot is formed between the upper guide edge and the lower guide edge for guiding a saw blade to perform a cutting procedure. The guide slot has a connecting member for connecting the upper guide edge and the lower guide edge.

According to the embodiment of the present invention, the extracorporeal alignment component has an engaging member, at least one aiming hole and an angle fixation hole. The engaging member is engaged with the connecting member. The aiming hole is used to confirm the direction of cutting. The angle fixation hole is disposed in the engaging member, the orientation/position of the universal osteotomy device is fixed to the bone by using an angle fixation bone pin.

According to the embodiment of the present invention, the aiming hole confirms the direction of cutting by passing through at least one aiming bone pin.

According to the embodiment of the present invention, the surfaces of the first body component and the second body component have a plurality of fixed holes.

According to the embodiment of the present invention, the universal osteotomy device is fixed on the surface of the bone by inserting at least one fixed bone pin in the plurality of fixed holes.

According to the embodiment of the present invention, wherein the upper guide edge extends outwardly from the first body component.

According to the embodiment of the present invention, wherein the lower guide edge extends outwardly from the second body component.

According to the embodiment of the present invention, wherein the first body component further comprises a first correcting through-hole. The first correcting through-hole is connected to the first body component by a first bar. The second body component further comprises a second correcting through-hole. The second correcting through-hole is connected to the second body component by a second bar.

According to the embodiment of the present invention, wherein the universal osteotomy device has at least one correction angle between at least one longitudinal axes of the first correcting through-hole and at least one longitudinal axis of the second correcting through-hole. When the open angle of the osteotomy is the same as that of the preoperative planning correction angle, the longitudinal axes of the first correcting through-hole and the corresponding longitudinal axis of the second correcting through-hole will coincide and pass through an alignment bar.

According to the embodiment of the present invention, wherein the correction angles are 1°-45°, preferably 3°-30°, the most preferably 6°-20°.

According to the embodiment of the present invention, wherein the depth of cutting from the upper guide edge and the lower guide edge to a cutting end point is 10 mm-90 mm, preferably 30 mm-90 mm, the most preferably 50 mm-90 mm.

According to the embodiment of the present invention, wherein the angle between the upper guide edge and the side guide edge is 1°-150°, preferably 60°-140°, the most preferably 90°-120°.

Compared with the conventional technique, the curvature of the surface of the universal osteotomy device is designed according to the average curvature or the uniform curvature of the surface of the target bone and made by three-dimensional printing (3D printing). Since the curvature of the surface of the universal osteotomy device is made with the average curvature or the uniform curvature of the target bone surface, so the universal osteotomy device can fit various bones of most patients, such as: tibia, femur, fibula, humerus, ulna, radius, clavicle, scapula and so on. The surgeon can perform the first cutting position under the guide slot specified by the device. The guide slot allows the surgeon to perform the operation accurately. It also provides a reference for calculating the angle and depth of cutting. The side guide edge provides the surgical reference of the surgeon at the second cutting position. The extracorporeal alignment component can take a non-invasive assessment of the angle when the surgery is performed, it can predict whether the orientation/position of the osteotomy device placement is correct and it can directly fix the osteotomy device on the bone. The extended barrier plate can avoid over-cutting. In addition, the curvature of the surface of the universal osteotomy device is made with the average curvature or the uniform curvature of the target bone surface. Therefore, it does not require preoperative assessment of the curvature of the patient's bone surface, it can be applied to the need for emergency surgery and the manufacturing process is simpler. The present invention further improves the original osteotomy device.

BRIEF DESCRIPTION OF THE DRAWINGS

FIG. 8 illustrates the depth of the present invention from the upper guide edge and the lower guide edge to the cutting end point.

The components, characteristics and advantages of the present invention may be understood by the detailed description of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims. The layout of components may be more complicated in practice.

Figure 1:
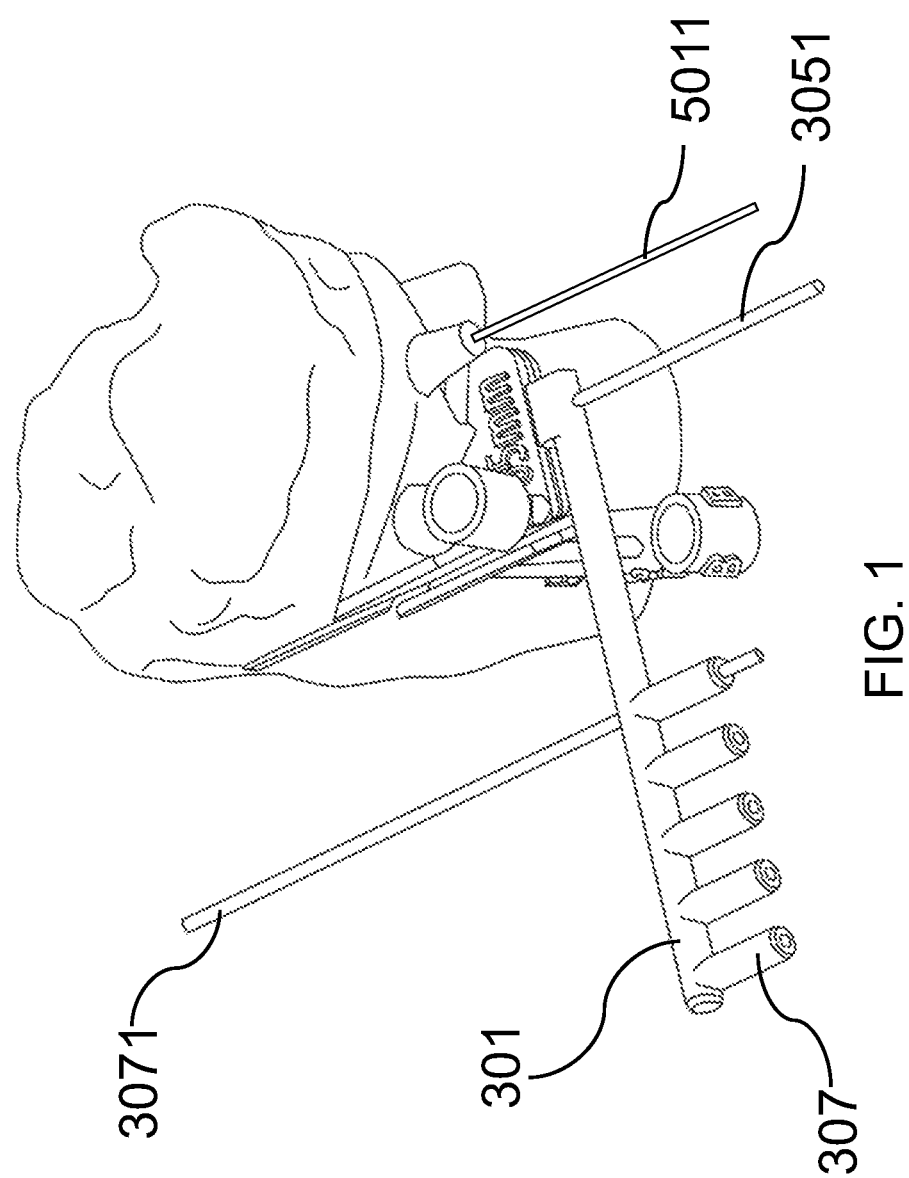
FIG. 1 illustrates a diagram of the universal osteotomy device placed on a bone.
Figure 2:
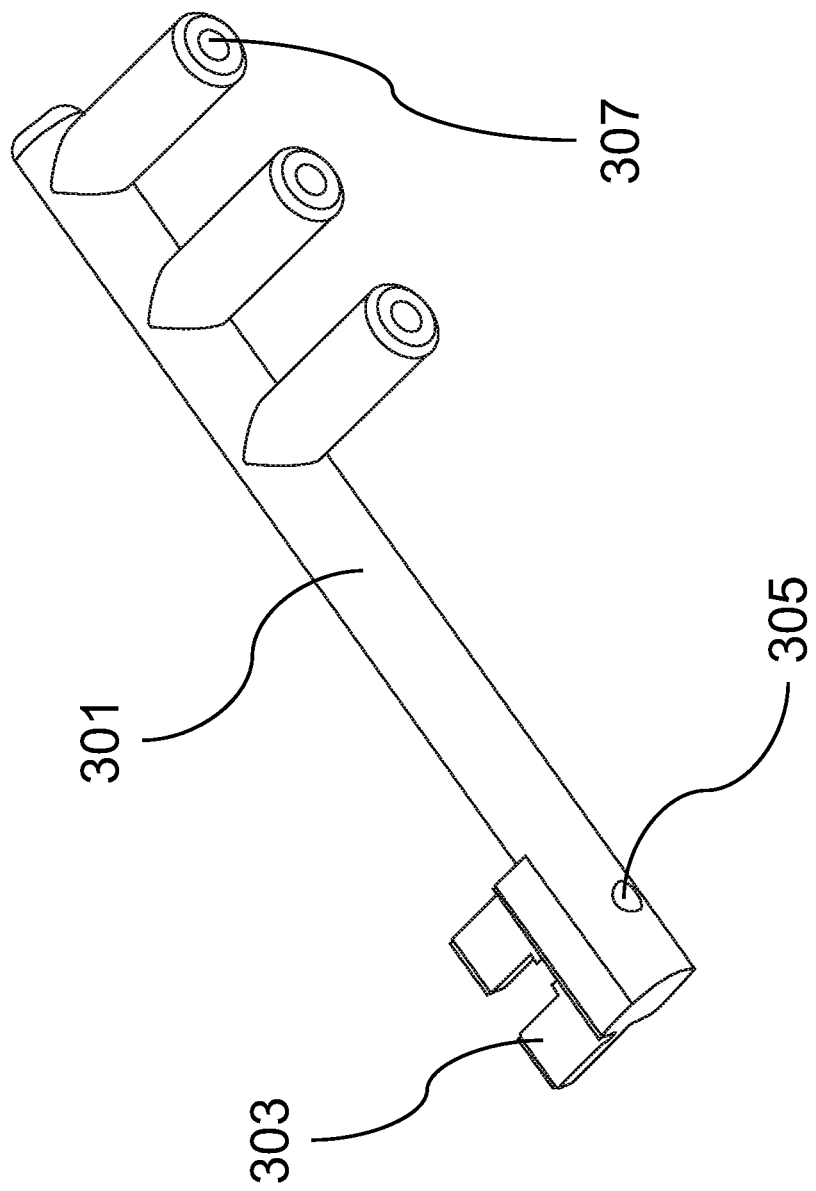
FIG. 2 illustrates a diagram of the extracorporeal alignment component.
Figure 3:
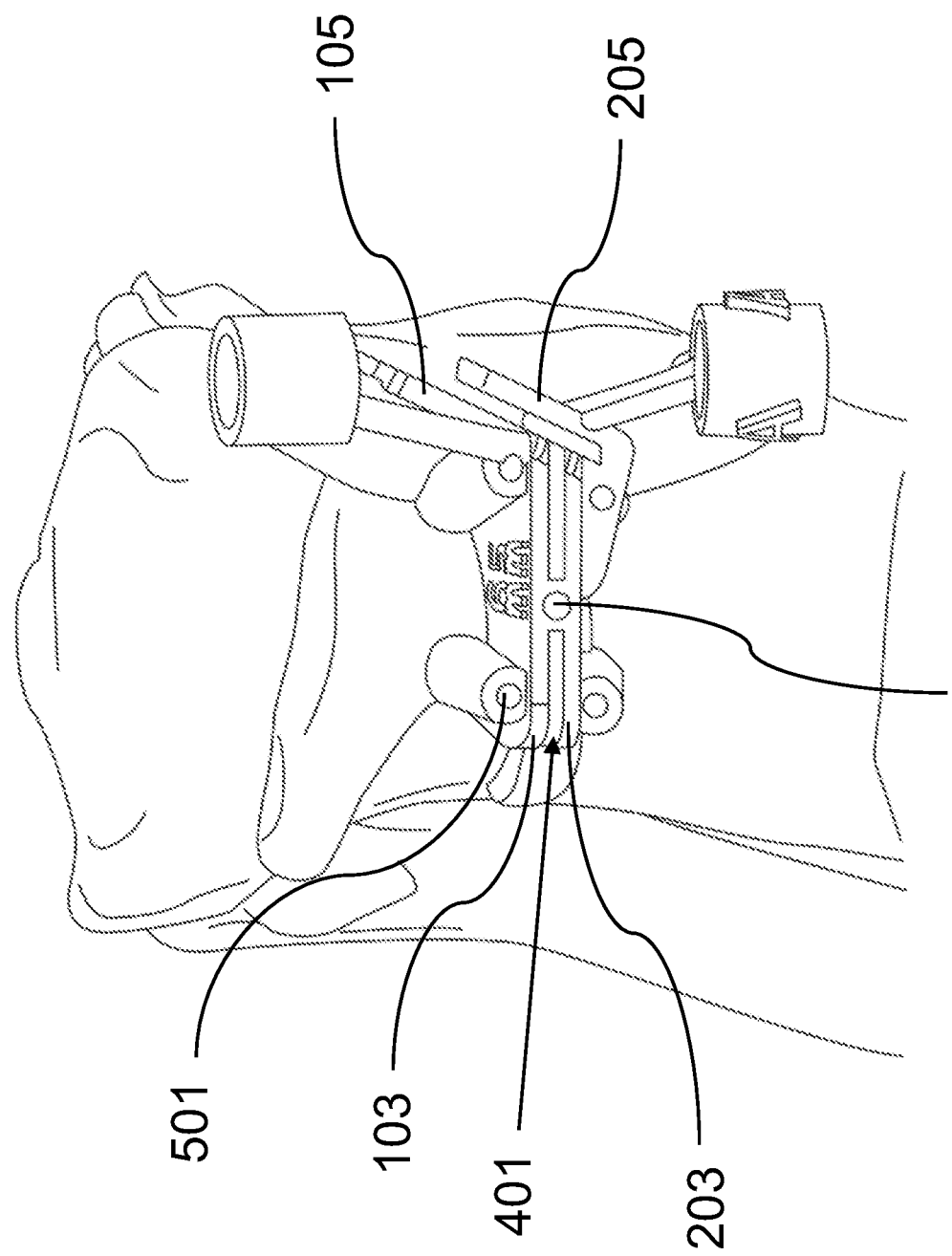
FIG. 3 illustrates a diagram of the universal osteotomy device without an extracorporeal alignment component.
Figure 4:
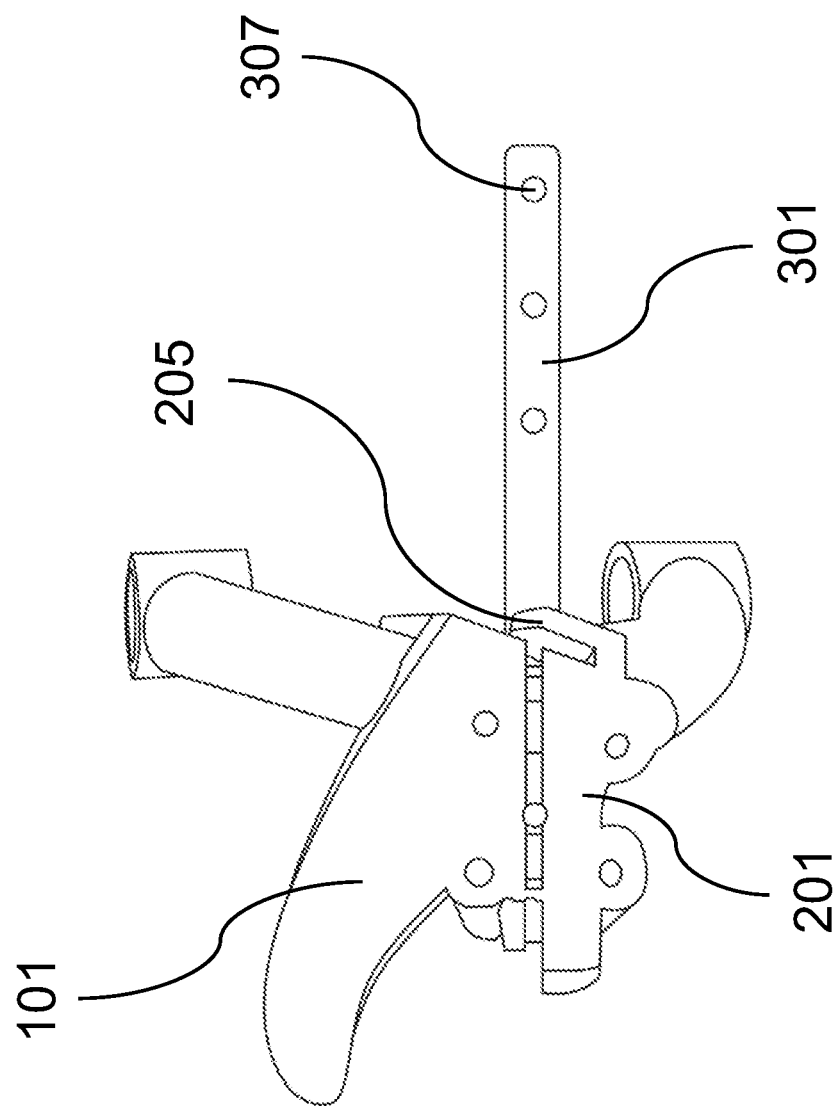
FIG. 4 illustrates a back view of the universal osteotomy device.

Please refer to FIG. 1, FIG. 2, FIG. 3 and FIG. 4. FIG. 1 illustrates a diagram of the universal osteotomy device placed on a bone. FIG. 2 illustrates a diagram of the extracorporeal alignment component 301. FIG. 3 illustrates a diagram of the universal osteotomy device without an extracorporeal alignment component 301. FIG. 4 illustrates a back view of the universal osteotomy device. The present invention provides a universal osteotomy device which can be used in various osteotomy, correction operation or reduction surgery. The universal osteotomy device can be used for other bones, such as: tibia, femur, fibula, humerus, ulna, radius, clavicle, scapula and so on. In the present embodiment, the universal osteotomy device is used to guide a saw blade to perform high tibial osteotomy of tibia. The universal osteotomy device comprises: a first body component 101, a second body component 201 and an extracorporeal alignment component 301. Wherein the first body component 101 has an upper guide edge 103 for forming a cutting track; the second body component 201 has a lower guide edge 203 disposed below the upper guide edge 103, a guide slot 401 is formed between the upper guide edge 103 and the lower guide edge 203 for guiding a saw blade to perform a cutting procedure. The guide slot 401 has a connecting member 403 for connecting the upper guide edge 103 and the lower guide edge 203. The extracorporeal alignment component 301 has an engaging member 303 and at least one aiming hole 307. The engaging member 303 is engaged with the connecting member 403. The aiming hole 307 is used to confirm the direction of cutting. Wherein the bone facing surface of the first body component 101 and the bone facing surface of the second body component 201 have an average curvature or a uniform curvature of the bone surface. When the operation is performed, the surgeon can directly cut the connecting member 403 with the bone saw.

When the universal osteotomy device is arranged on the surface of patient's tibia, the extracorporeal alignment component 301 is mounted on the connecting member 403 of the universal osteotomy device through the engaging member 303. The engaging member 303 and the aiming hole 307 are respectively located at both ends of the extracorporeal alignment component 301. When the universal osteotomy device is placed on the bone surface, the extracorporeal alignment component 301 has a rectangular appearance and it is placed laterally on the universal osteotomy device so that the aiming hole 307 can be located outside the human body. The orientation/position of placement of the universal osteotomy device can be evaluated in a noninvasive manner by the aiming hole 307. Therefore, it is possible to predict whether the orientation/position of the universal osteotomy device is correct. Then, the surgeon inserts the saw blade and starts cutting according to the cutting position guided by the upper guide edge 103 and the lower guide edge 203 of the universal osteotomy device. The surgeon can use the upper guide edge 103 and the lower guide edge 203 as a reference for the calculation of the depth of cut. In another way, make a mark on the saw blade, the surgeon can check the cutting depth by eyes.

In addition, the bone-facing surface of the first body component 101 and the bone-facing surface of the second body component 201 have an average curvature or a uniform curvature of the target bone surface and a uniform specification. So that the universal osteotomy device of the present invention can fit the bone surface of most patients and it is designed for medical emergencies. It can be used immediately in emergency and it does not require a complicated assessment before surgery. Thus, it is possible to achieve the accurate, rapid and convenient purpose for performing osteotomy.

In one embodiment of the present invention, the first body component 101 has an upper guide edge 103 and a side guide edge 105. The side guide edge 105 is disposed at the end of the upper guide edge 103 for forming a cutting track. The upper guide edge 103 and the lower guide edge 203 extend outwardly from the first body component 101 and the second body component 201, respectively. A guide slot 401 is formed between the upper guide edge 103 and the lower guide edge 203 for guiding the saw blade to perform a cutting procedure of the first cutting position. The side guide edge 105, located at one of side ends of the upper guide edge 103, is used to guide the saw blade to perform a cutting procedure of the second cutting position. The upper guide edge 103, the lower guide edge 203 and the side guide edge 105 are used to form the cutting track for operating high tibial osteotomy.

The surgeon can use the upper guide edge 103 and the lower guide edge 203 as a reference for the calculation of the depth of cut. The saw blade cuts to a predetermined depth and cuts along the upper guide edge 103 and the lower guide edge 203 to the inside of the human body. Then, it cuts off part of the tibia and cuts along the second cutting position guided by the side guide edge 105 to produce an oblique osteotomy.

In one embodiment of the present invention, the second body component 201 has a lower guide edge 203 and an extended barrier plate 205 located at one of side ends of the lower guide edge 203 corresponding to the side guide edge 105. The lower guide edge 203 disposed below the upper guide edge 103. The extended barrier plate 205 is disposed at the end of the lower guide edge 203 to prevent overcutting by the saw blade on the side guide edge 105. A guide slot 401 is formed between the upper guide edge 103 and the lower guide edge 203 for guiding a saw blade to perform a cutting procedure. The guide slot 401 has a connecting member 403 for connecting the upper guide edge 103 and the lower guide edge 203. In the previous technology of osteotomy device, it is found that the position of the side guide edge 105 often occurs over-cutting in the surgical operation. If the surgeon cuts more than a lot, the extra osteotomy will make the bones become more fragile. It may cause bones to break when fixing the bone plate. So that the patient's recovery period is prolonged. In order to avoid over-cutting, the present invention further improves the design. An extended barrier plate 205 is added to the second body component 201 relative to the side guide edge 105. When the saw blade cuts to a predetermined position, it can be blocked by the extended barrier plate 205 to avoid over-cutting. The entire cutting track becomes complete. In the practice of osteotomy, the present invention is carried out more precisely in accordance with the originally intended plan. It can prevent the occurrence of defects and shorten the recovery period of patients In another embodiment of the present invention, the extracorporeal alignment component 301 has an engaging member 303, at least one aiming hole 307 and an angle fixation hole 305. The engaging member 303 is engaged with the connecting member 403. The aiming hole 307 is used to confirm the direction of cutting. The angle fixation hole 305 is disposed in the engaging member 303, the orientation/position of the universal osteotomy device is fixed to the bone by using an angle fixation bone pin 3051. When the aiming hole 307 confirms that the orientation/position of the universal osteotomy device is correct, the universal osteotomy device can be fixed the orientation/position on the bone directly by inserting the angle fixation bone pin 3051 from the angle fixation hole 305 of the extracorporeal alignment component 301. Compared with the osteotomy device in the prior art, the present invention will have a more precise cutting angle and position. The precise cutting is a very important point in osteotomy. Because the open angle of the bone is based on it. Therefore, it affects the correction of the biomechanical axis of the low limb. The present invention can avoid ligament injury during surgery. It can also cut an osteotomy to resist the rotation of the bones due to the movement. The surgical procedure can be simplified, too.

In one embodiment of the present invention, the extracorporeal alignment component 301 has an engaging member 303 and at least one aiming hole 307. The engaging member 303 is engaged with the connecting member 403. The aiming hole 307 confirms the direction of cutting by passing through at least one aiming bone pin 3071. The aiming hole 307 is cylindrical in the present embodiment, but not limited to, it may be changed to other shapes as necessary. The aiming hole 307 is sequentially attached to the extracorporeal alignment component 301 by an end of the extracorporeal alignment component 301. Its cylindrical design allows the aiming bone pin 3071 to pass through. It is possible to determine whether the universal osteotomy device of the present invention is set at the correct orientation/position by the guidance of the aiming bone pin 3071. The aiming bone pin 3071 is the in vitro guideline of the orientation/position of the device. It is a non-invasive assessment In another embodiment of the present invention, the surfaces of the first body component 101 and the second body component 201 have a plurality of fixed holes 501, the universal osteotomy device is fixed on the surface of the bone by inserting at least one fixation bone pin 5011 in the plurality of fixed holes 501. In order to reinforce the fixation strength of the universal osteotomy device on the bone surface, at least one fixation bone pin 5011 may be inserted in the fixed holes 501 after the universal osteotomy device is fixed the orientation/position on the bone directly by inserting the angle fixation bone pin 3051 from the angle fixation hole 305 of the extracorporeal alignment component 301. Whereby the universal osteotomy device is fixed more firmly to the surface of the bone. It can avoid the saw blade causing the universal osteotomy device to move at the time of cutting. It makes the cutting position more accurate.

In one embodiment of the present invention, the upper guide edge 103 and the lower guide edge 203 extend outwardly from the first body component 101 and the second body component 201, respectively. A guide slot 401 is formed between the upper guide edge 103 and the lower guide edge 203 for guiding the saw blade to the first cutting position. The side guide edge 105 is used to guide the saw blade to the second cutting position. The upper guide edge 103, the lower guide edge 203 and the side guide edge 105 are used to form the cutting track. The saw blade cuts the tibia according to the first cutting position and the second cutting position for operating high tibial osteotomy.

Figure 5:
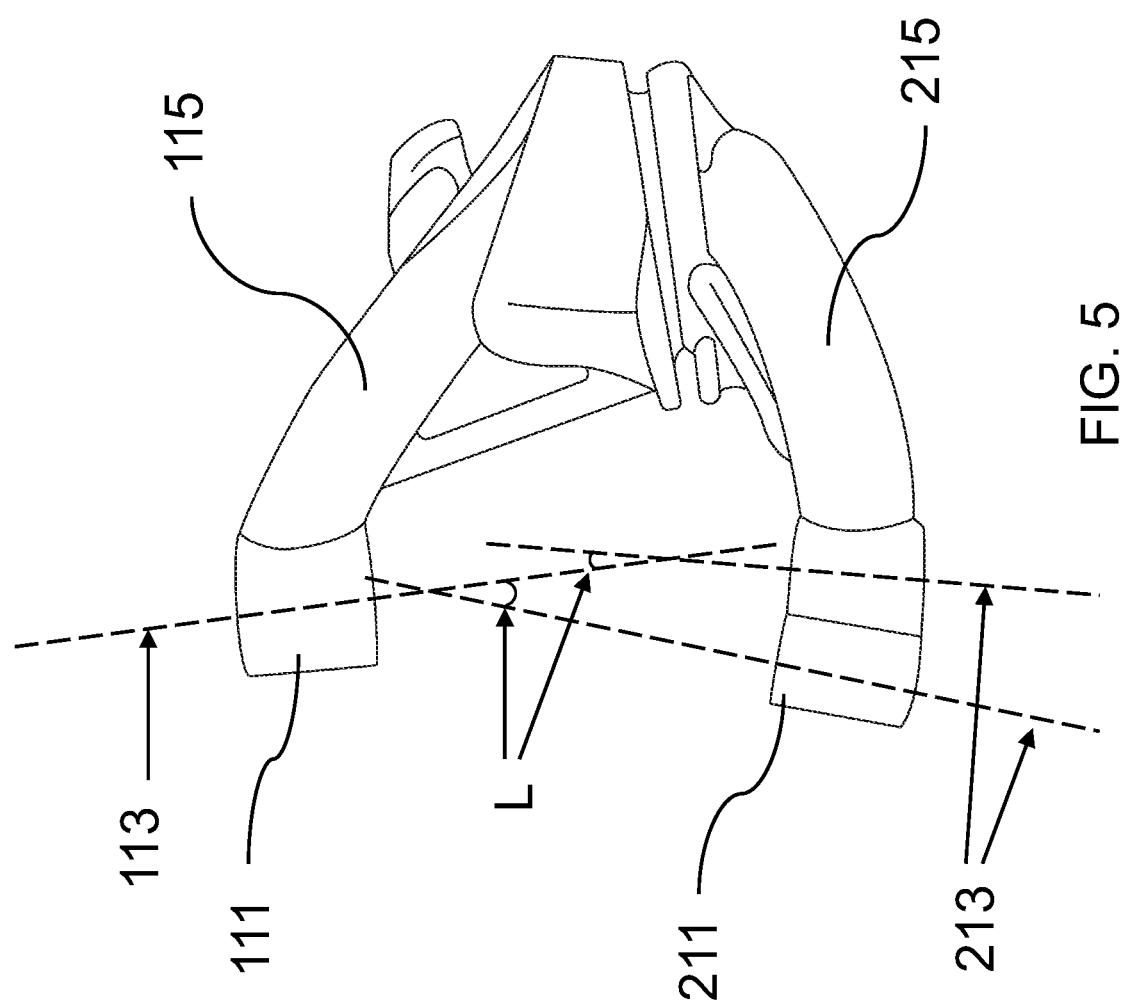
FIG. 5 illustrates a side view of the universal osteotomy device.
Figure 6:
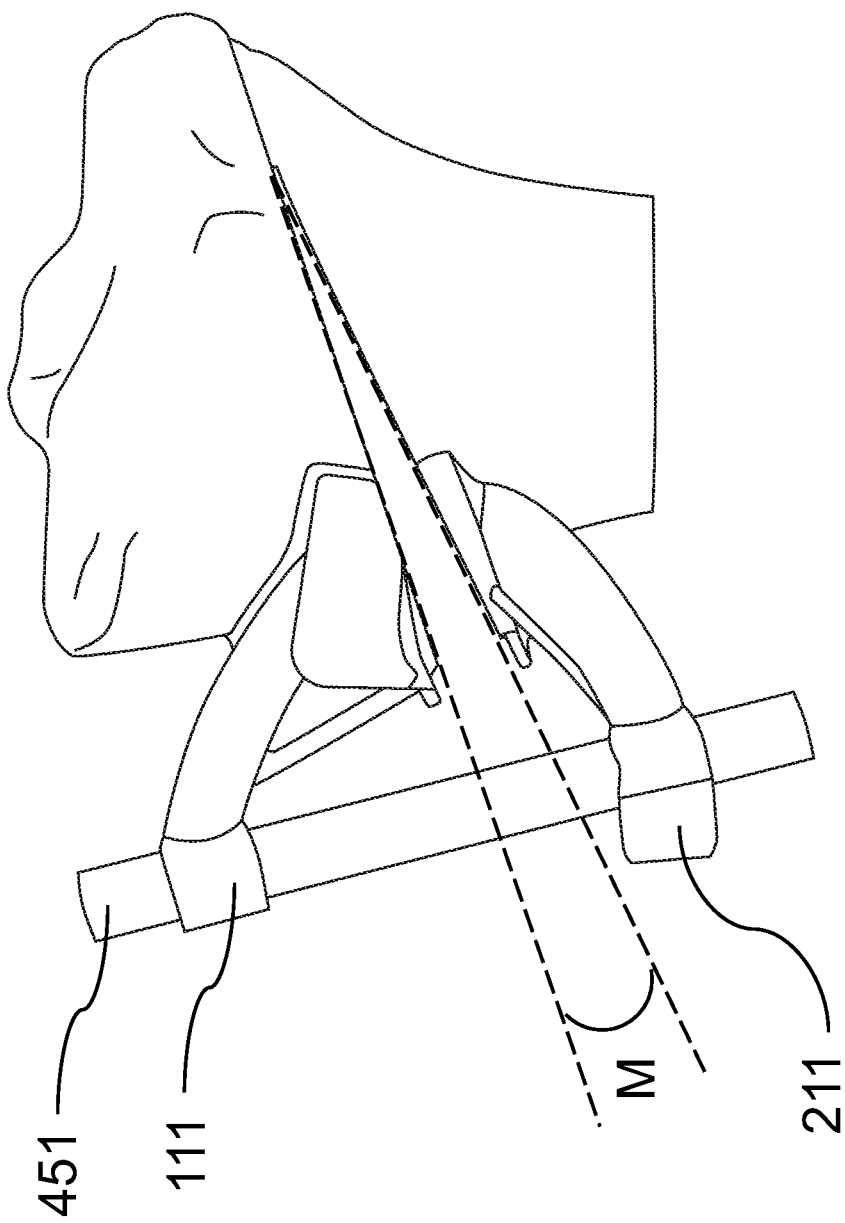
FIG. 6 illustrates that the bone is opened to the correction angle by the first body component and the second body component.
Figure 7:
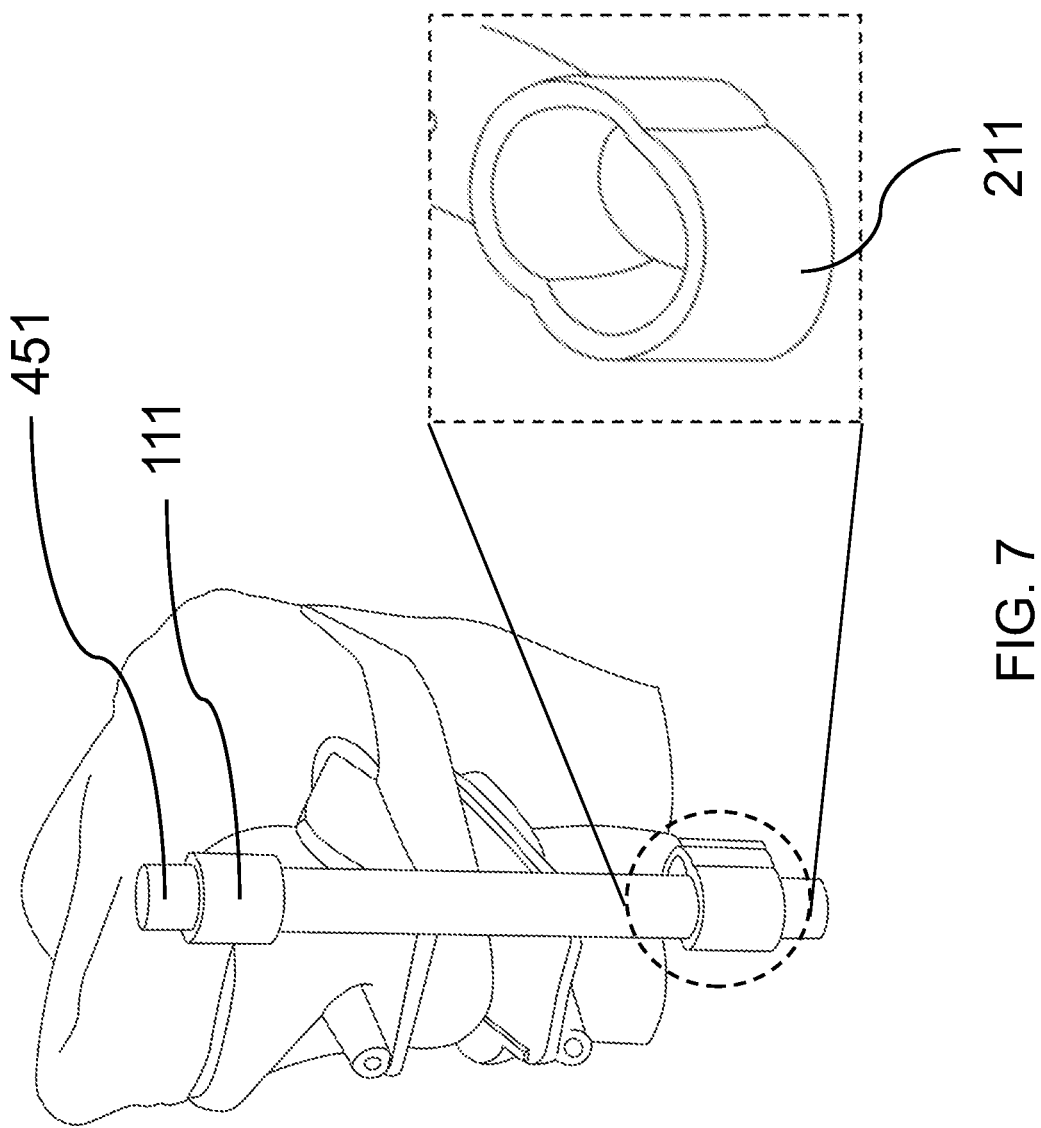
FIG. 7 illustrates that the bone is opened to another correction angle by the first body component and the second body component.

Please refer to FIG. 5, FIG. 6 and FIG. 7. FIG. 5 illustrates a side view of the universal osteotomy device. FIG. 6 illustrates that the bone is opened to the correction angle M by the first body component 101 and the second body component 201. FIG. 7 illustrates that the bone is opened to another correction angle M by the first body component 101 and the second body component 201. In another embodiment of the present invention, the first body component 101 further comprises a first correcting through-hole 111. The first correcting through-hole 111 is connected to the first body component 101 by a first bar 115. The second body component 201 further comprises a second correcting through-hole 211. The second correcting through-hole 211 is connected to the second body component 201 by a second bar 215. In the present invention, the first correcting through-hole 111 and the second correcting through-hole 211 are designed to confirm the angle at which the tibial osteotomy is opened in high tibial osteotomy. For this reason, there is at least one correction angle L between longitudinal axis 113 of the first correcting through-hole 111 and at least one longitudinal axis 213 of the second correcting through-hole 211. In high tibial osteotomy, an osteotomy of the osteotomy has a preoperative planning correction angle M. When the tibia is opened by the first body component 101 and the second body component 201 with the correction angle M, the longitudinal axes 113 of the first correcting through-hole 111 and the corresponding longitudinal axis 213 of the second correcting through-hole 211 can coincide. An alignment bar 451 is passed through the first correcting through-hole 111 and the second correcting through-hole 211 to ensure the correction angle M. Firstly, the size of the aforementioned correction angle M is based on the correction angle M that the tibia needs to open in high tibial osteotomy. Secondly, the angle between the longitudinal axes 113 of the first correcting through-hole 111 and the corresponding longitudinal axis 213 of the second correcting through-hole 211 is determined according to the desired correction angle M. The alignment bar 451 can be inserted between the first correcting through-hole 111 and the second correcting through-hole 211 only when the tibia is opened at a preoperative planned correction angle M by the first body component 101 and the second body component 201.

The saw blade cuts to a predetermined depth and cut along the upper guide edge 103 and the lower guide edge 203. Then, it cuts off part of the tibia and cuts along the second cutting position guided by the side guide edge 105 to produce an oblique osteotomy. After the osteotomy is cut, the first cutting position of the tibia is opened to the correction angle M of preoperative planning in the case where the universal osteotomy device is fixed to the tibia. The alignment bar 451 is then inserted through the first correcting through-hole 111 and the second correcting through-hole 211. After confirming the correction angle M of the surgical osteotomy of the tibia, the gap can be fixed to complete the operation.

As depicted in FIG. 7, two partial hollow cylindrical components, each has a through-hole with a hole size that is the same as the first through-hole 111, are joined together to form the second correcting through-hole 211. Since each partial hollow cylindrical components of the second correcting through-hole 211 has a hole axis, it is possible to form one longitudinal axis 113 or at least one longitudinal axis 213. At least one correction angle L between the longitudinal axis 113 and at least one longitudinal axis 213 are formed. The universal osteotomy device of the present invention can have different correction angles L since the correction angles L between the longitudinal axis 113 and the longitudinal axes 213 can be formed at different angles. It can reduce manufacturing costs in addition to expanding the scope of application.

Please refer to FIG. 8. illustrates the depth of the present invention from the upper guide edge 103 and the lower guide edge 203 to the cutting end point 601. In another embodiment of the present invention, wherein the correction angles L are 1°-45°, preferably 3°-30°, the most preferably 6°-20°; the depth of cutting from the upper guide edge 103 and the lower guide edge 203 to a cutting end point 601 is 10 mm-90 mm, preferably 30 mm-90 mm, the most preferably 50 mm-90 mm; the angle between the upper guide edge 103 and the side guide edge 105 is 1°-150°, preferably 60°-140°, the most preferably 90°-120°. The universal osteotomy device of the present invention can parameterize the correction angles L, the depth of cutting, the angle at which the upper guide edge 103 and the side guide edge 105 are formed. It is made in a large number of uniform specifications. Because it has many different parameters to choose from, it can cope with various emergencies. Furthermore, it can be used in line with the needs of patients immediately.

Compared with the conventional technique, the universal osteotomy device is manufactured by three-dimensional printing according to the average curvature or the uniform curvature of Asian skeletal surface collected before surgery. It constructs an integrally formed or combined solid instrument. The universal osteotomy device can fit the bones of most patients. The surgeon can perform the first cutting position under the guide slot 401 specified by the device. The guide slot 401 allows the surgeon to perform the operation accurately. It also provides a reference for calculating the angle and depth of cutting. The side guide edge 105 provides the surgical reference of the surgeon at the second cutting position. The extracorporeal alignment component 301 and the extended barrier plate 205 further improve the osteotomy device in the prior art. Therefore, the present invention can take a non-invasive assessment of the angle when the surgery is performed, it can predict whether the orientation/position of the osteotomy device placement is correct, it can directly fix the osteotomy device and it can avoid over-cutting. In addition to improving the surgery itself, the present invention also standardizes the implementation of the surgeon's operation.

Furthermore, the universal osteotomy device simplifies the prior art osteotomy device. It can significantly shorten the time of preoperative assessment. The curvature of the surface of the universal osteotomy device is made with the average curvature or the uniform curvature of the target bone surface. In addition to shortening the preoperative evaluation time, there is no need to spend extra design time. In the manufacturing process, the universal osteotomy device has a unified specification and shortens the overall manufacturing process. Therefore, the universal osteotomy device can be manufactured in large quantities and it can be used quickly. For emergency medical conditions, the universal osteotomy device provides an accurate, rapid and convenient way.

Various terms used in this disclosure should be construed broadly. For example, if an element "A" is to be coupled to or with element "B," element A may be directly coupled to element B or be indirectly coupled through, for example, element C. When the specification states that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification refers to "a" or "an" element, this does not mean there is only one of the described elements.

The foregoing descriptions are preferred embodiments of the present invention. As is understood by a person skilled in the art, the aforementioned preferred embodiments of the present invention are illustrative of the present invention rather than limiting the present invention. The present invention is intended to cover various modifications and similar arrangements included within the spirit and scope of the appended claims, the scope of which should be accorded the broadest interpretation so as to encompass all such modifications and similar structures.

We claim:

1. A universal osteotomy device comprising:
a first body component having an upper guide edge for forming a cutting track;
a second body component having a lower guide edge disposed below said upper guide edge,
a guide slot being formed between said upper guide edge and said lower guide edge for guiding a saw blade to perform a cutting procedure, said guide slot having a connecting member for connecting said upper guide edge and said lower guide edge;
wherein each said first body component and said second body component has a bone-facing surface with an average curvature or a uniform curvature of bone surface;
wherein said first body component further comprises a first correcting through-hole, said second body component further comprises a second correcting through-hole, at least one correction angle between one longitudinal axis of said first correcting through-hole and at least one longitudinal axis of said second correcting through-hole is formed.

2. The universal osteotomy device of claim 1, further comprising:
an extracorporeal alignment component having an engaging member and at least one aiming hole, said engaging member being engaged with said connecting member, said aiming hole confirming the direction of cutting by passing through at least one aiming bone pin.

3. The universal osteotomy device of claim 2, said first body component further comprising:
a side guide edge being disposed at one of side ends of said upper guide edge for forming a cutting track.

4. The universal osteotomy device of claim 3, said second body component further comprising:
an extended barrier plate being disposed at one of side ends of said lower guide edge corresponding to said side guide edge of said upper guide edge to prevent over-cutting by said saw blade on said side guide edge.

5. The universal osteotomy device of claim 4, said extracorporeal alignment component further comprising:
an angle fixation hole being disposed in said engaging member, an orientation of said universal osteotomy device being fixable to a bone by using an angle fixation bone pin.

6. The universal osteotomy device of claim 5, wherein said first correcting through-hole is connected to said first body component by a first bar; said second correcting through-hole is connected to said second body component by a second bar.

7. The universal osteotomy device of claim 6, when an open angle of osteotomy is the same as that of a preoperative planning correction angle, said longitudinal axis of said first correcting through-hole and a corresponding longitudinal axis of said second correcting through-hole will coincide and pass through an alignment bar.

8. The universal osteotomy device of claim 7, wherein said at least one correction angles, each has an angle in a range of 1°-45°.

9. The universal osteotomy device of claim 8, wherein a depth of cutting from said upper guide edge and said lower guide edge to a cutting end point is 10 mm-90 mm.

10. The universal osteotomy device of claim 9, wherein an angle between said upper guide edge and said side guide edge is in a range of 1°-150°.

\* \* \* \* \*